United States Patent
Stadler et al.

(10) Patent No.: US 11,504,309 B2
(45) Date of Patent: *Nov. 22, 2022

(54) DEO EMULSION FOR AEROSOLS, DEODORANT COMPRISING THE SAME AND USE OF THE DEODORANT

(71) Applicant: Henkel AG & Co. KGaA, Duesseldorf (DE)

(72) Inventors: Iris Marina Stadler, Duesseldorf (DE); Daniel Solich, Langenfeld (DE); Inga Kerstin Vockenroth, Duesseldorf (DE)

(73) Assignee: HENKEL AG & CO. KGAA, Duesseldorf (DE)

(*) Notice: Subject to any disclaimer, the term of this patent is extended or adjusted under 35 U.S.C. 154(b) by 0 days.

This patent is subject to a terminal disclaimer.

(21) Appl. No.: 17/039,093

(22) Filed: Sep. 30, 2020

(65) Prior Publication Data

US 2021/0093520 A1 Apr. 1, 2021

(30) Foreign Application Priority Data

Sep. 30, 2019 (DE) .................... 10 2019 126 252.6

(51) Int. Cl.
| | | |
|---|---|---|
| *A61K 8/04* | (2006.01) | |
| *A61K 8/23* | (2006.01) | |
| *A61K 8/34* | (2006.01) | |
| *A61K 8/37* | (2006.01) | |
| *A61K 8/86* | (2006.01) | |
| *A61K 8/891* | (2006.01) | |
| *A61Q 15/00* | (2006.01) | |

(52) U.S. Cl.
CPC .............. *A61K 8/046* (2013.01); *A61K 8/04* (2013.01); *A61K 8/23* (2013.01); *A61K 8/34* (2013.01); *A61K 8/345* (2013.01); *A61K 8/347* (2013.01); *A61K 8/37* (2013.01); *A61K 8/86* (2013.01); *A61K 8/891* (2013.01); *A61Q 15/00* (2013.01); *A61K 2800/30* (2013.01); *A61K 2800/77* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 2003/0021847 A1* | 1/2003 | Baxter | A61K 8/345 424/487 |
| 2016/0089321 A1* | 3/2016 | Anconi | A61K 8/58 424/67 |
| 2017/0333319 A1* | 11/2017 | Doering | A61K 8/416 |
| 2018/0168947 A1 | 6/2018 | Banowski et al. | |
| 2019/0336434 A1* | 11/2019 | Li | A61K 8/0216 |

FOREIGN PATENT DOCUMENTS

| | | |
|---|---|---|
| DE | 102014221673 A1 | 4/2016 |
| DE | 102016225736 A1 | 6/2018 |
| FR | 3051358 A1 | 11/2017 |
| FR | 3061429 A1 | 7/2018 |
| GB | 2555506 A | 5/2018 |
| WO | 2018122209 A1 | 7/2018 |

OTHER PUBLICATIONS

Lem et al ("Selecting the perfect silicone for your formulation", an internet article obtained from the website : https://www.personalcaremagazine.com/story/13149/selecting-the-perfect-silicone-for-your-formulation (Jul. 9, 2014)) (Year: 2014).*

\* cited by examiner

*Primary Examiner* — Sin J Lee
(74) *Attorney, Agent, or Firm* — Lorenz & Kopf, LLP

(57) ABSTRACT

The present disclosure concerns a deodorant emulsion for an aerosol spray which is free from aluminum salts and ethanol, comprising: at least one emulsifier, at least one salt, water, at least one silicone oil and at least one further oil, and a deodorant aerosol spray product comprising a pressure or pump spray container with spray head, the filling of which comprises the deodorant emulsion and optionally a propellant and/or further solvent, and a use of the deodorant aerosol spray product for deodorizing human skin.

18 Claims, No Drawings

DEO EMULSION FOR AEROSOLS, DEODORANT COMPRISING THE SAME AND USE OF THE DEODORANT

CROSS-REFERENCE TO RELATED APPLICATION

This application claims priority to German Patent Application No. 10 2019 126 252.6, filed Sep. 30, 2019, which is incorporated herein by reference in its entirety.

TECHNICAL FIELD

The present disclosure relates to a deodorant emulsion for topical treatment of the skin, comprising an emulsifier, a salt, water, a silicone oil, and further oils, wherein the deodorant emulsion contains no aluminum salt and no ethanol.

BACKGROUND

Washing, cleaning, and caring for your own body is a basic human need. The manufacturers of body hygiene products are constantly trying to meet these human needs in a variety of ways. Particularly important for daily hygiene is the continuous elimination or preventive prevention of the development of unpleasant body odor. Numerous special deodorizing body care products as well as body care products with antiperspirant effect are known in the state of the art, which were developed for the application in body care emitter with a high density of sweat glands, especially the armpit region or for example also the feet or palms of the hands.

Body odor is largely caused by the bacterial decomposition of individual components of sweat on the skin. When deodorizing the body, a rough distinction can be made between active substances that absorb or cover up substances that have already developed an unpleasant odor, e.g. activated carbon, zinc ricinoleate, cyclodextrins and ion exchangers, e.g. fragrances and perfumes, and active substances that prevent or at least slow down the decomposition of sweat and the development of unpleasant smelling substances, e.g. germ-inhibiting substances, prebiotically active components and enzyme inhibitors. Depending on the selected mechanism by which body odor is to be prevented, odor absorbers, fragrances, deodorizing ion exchangers, germ-inhibiting agents, prebiotically active components, enzyme inhibitors and other active substances can be used as cosmetic deodorizing agents. The active substances must be contained in the compositions, while ensuring that the compositions can be conveniently supplied in a desired pharmaceutical form and that the compositions do not cause an unpleasant feeling on the skin.

Many state-of-the-art cosmetic antiperspirants used for perspiration and/or odor inhibition often contain aluminum and/or zirconium compounds as antiperspirant agents. On the one hand, these antiperspirant compounds reduce the body's sweat secretion by temporarily narrowing and/or clogging the ducts of the sweat glands, so that the amount of sweat can be reduced by from about 20 to about 60 percent. On the other hand, they have an additional deodorizing effect due to their antimicrobial effect.

However, the aluminum and/or zirconium compounds used to inhibit perspiration can lead to unpleasant skin reactions for some users. Aluminum compounds are often viewed critically by consumers. It has therefore become largely undesirable to use aluminum in cosmetic products, as there is a warning against excessive aluminum absorption into the human body due to the possibility of a health hazard. Aluminum, especially from aluminum salts, can be absorbed through the skin, sometimes with considerably better bioavailability than aluminum inevitably contained in food. For this reason, even some rather conservative officials or organizations dedicated to public health advise against the use of aluminum-containing cosmetics. In addition, the use of the antiperspirant compounds can lead to staining of clothing.

Furthermore, many users consider ethanol-free cosmetics to be desirable as ethanol is associated with skin dehydration and other skin irritation reactions. The technical field of this present disclosure is often referred to as non-alcoholic products, compositions, etc., although strictly speaking only ethanol-free products are meant, which may contain other alcohols. This terminology is not deviated from here. Thus, when a product or composition is described as alcohol-free, free of alcohols or similar, this should mean that no ethanol is contained, but other alcohols may be contained, unless explicitly stated otherwise at the appropriate place.

Sprays are a market-dominating category in the deodorant sector. Such products are therefore preferred by many users over sticks, roll-on deodorants, and other packaging. However, sprays pose challenges about the formulation of a deodorant, among other things because the propellants usually used are not compatible with many formulations, especially emulsions.

BRIEF SUMMARY

The task underlying the present disclosure is thus to provide a deodorant emulsion which is free from aluminum salts and ethanol and which is suitable for an aerosol spray, as well as a corresponding spray product and its use.

Deodorant emulsions, deodorant aerosol spray products, and methods of using the same are provided herein. In an embodiment, a deodorant emulsion includes:
  at least one emulsifier,
  at least one salt,
  water,
  at least one silicone oil, and
  at least one further oil;
  wherein the deodorant emulsion is free from aluminum salts and ethanol.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The task underlying the present disclosure is thus to provide a deodorant emulsion which is free from aluminum salts and ethanol and which is suitable for an aerosol spray, as well as a corresponding spray product and its use.

The task underlying the present disclosure is solved by the subjects described in detail below.

A deodorant emulsion for an aerosol spray which is free from aluminum salts and ethanol, comprising at least one emulsifier, at least one salt, water, at least one silicone oil and at least one other oil.

A deodorant emulsion within the meaning of this patent application is an emulsion containing only cosmetically acceptable ingredients. Otherwise, it is, according to the common definition of an emulsion, a finely divided mixture of two normally immiscible liquids without visible segregation, in which a finely divided mixture of two liquids, such as oil and water, is present. A liquid, in this context also called phase, forms small droplets, distributed in the other liquid. The phase that forms droplets is called internal phase or disperse phase. The phase in which the droplets float is called outer phase or continuous phase. Emulsions belong to the disperse systems and differ from mixtures of mixable liquids, such as ethanol and water. Emulsions are usually cloudy, milky liquids. As contemplated herein preferred deodorant emulsions are in the form of a water-in-silicone emulsion.

Until now, oil sprays were the usual products in the deodorant category of aerosol sprays, which dominates the market. However, it may be desirable to use an emulsion for a deodorant instead of a mixture with predominantly oily properties. This is desirable, for example, because certain ingredients cannot be worked into an oil spray but into an emulsion. However, the use of emulsions is made more difficult by the fact that they tend to be unstable and tend to separate back into their original phases. With the formulation described here, however, the inventors have found a way to produce an emulsion that is stable even in the presence of propellant gases and is therefore suitable for use in an aerosol spray. This stability is not only given in the presence of propellants, but also in the presence of common deodorants. The emulsion is also well-tolerated and can, for example, be applied directly after shaving without causing skin reactions and creates a pleasant feeling on the skin, especially no feeling of stickiness or oiliness. Furthermore, the emulsion is easy to spray. An emulsion also offers advantages in terms of resource consumption, as it typically includes a significant proportion of water instead of heavy and energy-intensive oily components. This is not only resource-saving in the provision of raw materials but also in wastewater treatment, which can be more effective with less pollution and with less energy input. Therefore, the deodorant emulsion as contemplated herein is advantageous under several aspects in terms of environmental protection.

Furthermore, it can be advantageous that the deodorant emulsion for an aerosol spray is free of aluminum salts and ethanol. Ethanol can dry out the skin or cause other skin irritations and aluminum in deodorant products is sometimes not desired by users as human intake of aluminum should not exceed a certain level and, especially freshly shaved skin, allows aluminum to be absorbed from an applied cosmetic product.

The present disclosure concerns embodiments based on a carrier comprising water or a water/alcohol mixture. Preferably the aqueous or aqueous-alcoholic carrier water or a water/alcohol mixture, the alcohol preferably being selected from a linear or branched alcohol such as, propanol, isopropanol, propanediol-1.3, dipropylene glycol, propanediol-12, propanediol-1.2. Preferably, water or the water/alcohol mixture is contained in an amount from about 60%-to about 99-%, by weight, more preferably from about 65%-to about 96-% by weight, most preferably from about 70%-to about 90-% by weight, based on the total weight of the deodorant emulsion.

It is preferred that the deodorant emulsion for an aerosol spray comprises from about 0.5%-to about 5.0%-by weight, further preferably from about 1.0%-to about 4.5%-by weight, more preferably from about 2.0%-to about 4.0%-by weight of the at least one emulsifier, based on the total weight of the deodorant emulsion for an aerosol spray.

The advantageous properties described above are particularly pronounced in these concentration ranges and there is a particularly wide scope for shaping other parameters of the deodorant emulsion. Cosmetically acceptable emulsifiers are for example alkoxylated fatty acid alcohols like C14 to C18 alcohols with two to 22 ethoxy groups, for example steareth-2 or steareth-21, or PPG-15 stearyl ether. In the context of this present disclosure, a product commercially available as "Dow Corning ES-5227 DM Formulation Aid" is particularly preferred. It is a silicone emulsifier to produce low to medium viscosity water-in-silicone emulsions for a variety of applications such as color cosmetics, skin care, sun care, antiperspirants, and deodorants. It is an ethoxylated and propoxylated silicone emulsifier. Its main function is the production of water-in-silicone emulsions with textures from lotion to cream. It is a 25% dispersion of silicone polyether in a low viscosity, non-volatile dimethicone liquid. (INCI designation) Dimethicone (and) PEG/PPG-18/18 Dimethicone.

It is preferred that the deodorant emulsion for an aerosol spray comprises from about 0.1%-to about 10.0%-by weight, further preferably from about 0.5%-to about 7.0%-by weight, more preferably from about 1.0%-to about 5.0%-by weight of the at least one salt, based on the total weight of the deodorant emulsion for an aerosol spray.

Salts can fulfill various functions in deodorant emulsions. They can have an emulsion-stabilizing effect, can be antiperspirant or antibacterial, but are also used as moisturizers or in other functions. Their beneficial effects are particularly pronounced in the concentration ranges defined here. In principle, cosmetically acceptable salts may be used as long as they are not explicitly excluded here, for example silver salts such as silver citrate, dihydrogen silver citrate, silver lactate and silver sulphate, soluble complex salts of silver, colloidal silver and silver zeolites. However, magnesium sulphate is particularly preferred for the purposes of this present disclosure, as it acts, inter alia, as an emulsion stabilizer.

It is preferred that the deodorant emulsion for an aerosol spray comprises from about 1.0%-to about 20.0%-by weight, further preferably from about 3.0%-to about 17.0%-by weight, more preferably from about 5.0%-to about 15.0%-by weight, of at least one silicone oil, based on the total weight of the deodorant emulsion for an aerosol spray.

The silicone oil may be selected from linear silicone oils, especially polydimethylsiloxane, and cyclic silicone oils, especially cyclopentasiloxane. Silicone oils give a pleasant silky skin feeling. Linear polydimethylsiloxanes bear the INCI designation Dimethicone. The chain length of the dimethylsiloxane chain determines the viscosity of the polydimethylsiloxanes. For the characterization of polydimethylsiloxanes or dimethicones their kinematic viscosity is therefore often given, usually in the unit centiStokes (cSt).

It is preferred that the deodorant emulsion for an aerosol spray comprises from about 1.0%-to about 20.0%-by weight, further preferably from about 6.0%-to about 17.0%-by weight, more preferably from about 11.0%-to about 15.0%-by weight of the at least one other oil, based on the total weight of the deodorant emulsion for an aerosol spray.

The oil is involved in the formation of the oil phase. For example, the oil may be selected from paraffins, isoparaffins, polypropylene glycol ethers, polyethylene glycol ethers, organic esters, ethers, and ether carbonates. But basically, any cosmetically acceptable oil can be used.

On the one hand, the oil has the function of allowing certain ingredients to be incorporated into the deodorant emulsion, on the other hand it cares for the skin.

The oil phase may preferably contain particulate substances. Particularly suitable are fumed silica or layered silicates, which are modified to be even more hydrophobic.

The particulate substances serve as thickeners and stabilizers. Hydrophobically modified bentonites and/or hydrophobically modified hectorites are particularly preferred.

It is preferred that the deodorant emulsion for an aerosol spray comprises at least one perfume oil, further preferably in a concentration of from about 1.0%-to about 10.0%-by weight, further preferably from about 2.0%-to about 8.0%-by weight, more preferably from about 3.0%-to about 7.0%-by weight of the at least one perfume oil, based on the total weight of the deodorant emulsion for an aerosol spray.

A perfume oil comprises one or more scents or fragrances. The definition of a fragrance for the purposes of the present application corresponds to the usual professional definition as given by RÖMPP Chemie Lexikon ('Römpp Lexikon Chemie', J. Falbe, M. Regitz (eds.), 10th edition, Thieme-Verlag). Examples of fragrance and aromatic compounds of the ester type are benzyl acetate, phenoxyethyl isobutyrate, p-tert. butylcyclohexyl acetate, linalyl acetate, dimethylbenzylcarbinyl acetate (DMBCA), phenylethyl acetate, benzyl acetate, ethylmethylphenylglycinate, allylcyclohexyl propionate, styrenallylpropionate, benzyl salicylate, cyclohexyl salicylate, floramate, melusate and jasmecyclate. Examples of fragrance and aromatic compounds of the ether type are benzyl ethyl ether and ambroxane, examples of fragrance and aromatic compounds of the aldehyde type are the linear alkanals with 8-18 C atoms, citral, citronellal, citronellyloxy-acetaldehyde, cyclamenaldehyde, lily and bourgeonal, examples of odoriferous compounds of the ketone type are jonones, alpha-isomethylionone and methylcedryl ketone, examples of odoriferous compounds of the alcohol type are anethole, citronellol, eugenol, geraniol, linalool, phenylethyl alcohol and terpineol, examples of odoriferous compounds of the terpene type are limonene and pinene. Examples of fragrance and scent compounds are pine, citrus, jasmine, patchouli, rose, ylang ylang oil, muscatel sage oil, chamomile oil, clove oil, mint oil, cinnamon leaf oil, lime blossom oil, juniper berry oil, vetiver oil, olibanum oil, galbanum oil, labdanum oil, orange blossom oil, neroli oil, orange peel oil and sandalwood oil, furthermore the essential oils like angelica root oil, anise oil, arnica blossom oil, basil oil, bay oil, bergamot oil, champaca blossom oil, silver fir oil, silver fir cone oil, elemi oil, eucalyptus oil, fennel oil, spruce needle oil, geranium oil, ginger grass oil, guaiac wood oil, gurjun balsam oil, helichrysum oil, ho-oil, ginger oil, Iris oil, cajeput oil, calamus oil, chamomile oil, camphor oil, canaga oil, cardamom oil, cassia oil, pine needle oil, copaïva balsam oil, coriander oil, spearmint oil, caraway oil, cumin oil, lavender oil, lemongrass oil, lime oil, tangerine oil, lemon balm oil, musk seed oil, myrrh oil, clove oil, niaouli oil, orange oil, origanum oil, Palmarosa oil, patchouli oil, Peru balsam oil, petitgrain oil, pepper oil, peppermint oil, pimento oil, pine oil, rose oil, rosemary oil, sandalwood oil, celery oil, spik oil, star anise oil, turpentine oil, thuja oil, thyme oil, verbena oil, juniper berry oil, wormwood oil, wintergreen oil, hyssop oil, cinnamon oil, citronella oil, lemon oil and cypress oil. Other fragrance and aroma compounds are ambrettolide, alpha-amyl cinnamaldehyde, anethole, anisaldehyde, anise alcohol, anisole, methyl anthranilic acid ester, acetophenone, benzyl acetone, benzaldehyde, ethyl benzoate, benzophenone, benzyl alcohol, benzyl acetate, benzyl benzoate, benzyl formate, benzyl valerianate, borneol, bornyl acetate, alpha-bromostyrene, n-decylaldehyde, n-dodecyl aldehyde, eugenol, eugenol methyl ether, eucalyptol, farnesol, fenchone, fenchyl acetate, geranyl acetate, geranyl formate, heliotropin, methyl heptanecarboxylate, heptaldehyde, hydroquinone dimethyl ether, hydroxycinnamic aldehyde, hydroxycinnamic alcohol, indole, iron, isoeugenol, isoeugenol methyl ether, isosafrol, jasmone, camphor, carvacrol, carvone, p-cresol methyl ether, coumarin, p-methoxyacetophenone, methyl-n-amylketone, methyl anthranilic acid methyl ester, p-methylacetophenone, methylchavicol, p-methylquinoline, methyl-β-naphthylketone, methyl-n-nonyl acetaldehyde, Methyl-n-nonylketone, muscone, β-naphthol ethyl ether, β-naphthol methyl ether, nerol, nitrobenzene, n-nonylaldehyde, nonylacohol, n-octylaldehyde, p-oxy-acetophenone, pentadecanolide, β-phenylethyl alcohol, phenylacetaldehyde dimethyacetal, phenylacetic acid, pulegone, safrole, isoamyl salicylic acid ester, methyl salicylic acid ester, hexyl salicylic acid ester, cyclohexyl salicylic acid ester, Santalol, skatole, terpineol, thyme, thymol, γ-undecalactone, vanillin, veratrum aldehyde, cinnamic aldehyde, cinnamic alcohol, cinnamic acid, ethyl cinnamate and benzyl cinnamate. Other (more volatile) fragrances are alkyl isothiocyanates (alkyl legumes), butanedione, limonene, linalool, linayl acetate and propionate, menthol, menthone, methyl-n-heptenone, phellandrene, phenylacetaldehyde, terpinyl acetate, citral and citronellal. A particularly preferred perfume oil in the context of the present disclosure is the commercially available product "Parfum Crispy Grapefruit A T12033987".

A perfumed deodorant has the advantage that it not only reduces or prevents the emergence and/or spread of bad smelling substances, but also gives the wearer a subtle pleasant scent without the need to use another product.

It is preferred that the deodorant emulsion for an aerosol spray comprises at least one deodorant active ingredient, further preferably in a concentration of from about 0.1%-to about 50.0%-by weight, further preferably from about 0.5%-to about 40.0%-by weight, particularly preferably from about 1.0%-to about 30.0%-by weight of the at least one deodorant active ingredient, based on the total weight of the deodorant emulsion for an aerosol spray.

Antimicrobial, antibacterial, or germ-inhibiting substances, antioxidants, odor adsorbents or enzyme inhibitors can be used as such additional deodorants or deodorant active ingredients. Suitable antimicrobial, antibacterial, or germ-inhibiting substances are in particular organohalogen compounds as well as organohalides, quaternary ammonium compounds and several plant extracts. Preferred are halogenated phenol derivatives such as hexachlorophene or Irgasan DP 300 (triclosan, 2,4,4'-trichloro-2'-hydroxydiphenyl ether), 3,4,4'-trichlorocarbanilide, chlorhexidine (1,1'-hexamethylene-bis-[5-(4-chlorophenyl)]-biguanide), chlorhexidine gluconate, benzalkonium halides and cetylpyridinium chloride. Furthermore, sodium bicarbonate and sodium phenolsulfonate as well as e.g. the components of lime blossom oil can be used. Weaker antimicrobial substances, which however have a specific effect against the gram-positive germs responsible for sweat decomposition, can also be used as deodorant agents. Benzyl alcohol can also be used as deodorant active ingredient. Other antibacterial deodorants are lantibiotics, glycoglycerolipids, sphingolipids (ceramides), sterols and other active ingredients that inhibit bacterial adhesion to the skin, e.g. glycosidases, lipases, proteases, carbohydrates, di- and oligosaccharide fatty acid esters and alkylated mono- and oligosaccharides. Preferred deodorant active ingredients are long-chain diols, e.g. 1,2-alkane-(C5-C18) diols, glycerol mono(C8-C18) fatty acid esters or, particularly preferred, glycerol mono (C6-C16) alkyl ethers, especially 2-ethylhexyl glycerol ethers, which are very well tolerated by the skin and mucous membranes and are effective against corynebacteria, and also phenoxyethanol, phenoxyisopropanol (3-phenoxy-propan-2-ol), anisyl alcohol, 2-methyl-5-phenyl-pentan-1-ol, 1,1 dimethyl-3-phenyl-propan-1-ol, benzyl alcohol, 2-phenylethane-1-ol, 3-phenylpropane-1-ol, 4-phenyl-butan-1-ol, 5-phenylpentane-1-ol, 2-Benzylheptan-1-ol, 2,2-dimethyl-3-phenyl-1-ol, 2,2-Dimethyl-3-(3'-methylphenyl) propan-1-ol, 2-ethyl-3-phenylpropan-1-ol, 2-ethyl-3-(3'-methylphenyl) propan-1-ol, 3-(3'-chlorophenyl)-2-ethylpropane-1-ol, 3-(2'-chlorophenyl)-2-ethylpropane-1-ol, 3-(4'-chlorophenyl)-2-ethylpropane-1-ol, 3-(3',4'-dichlorophenyl)-2-ethylpropane-1-ol, 2-Ethyl 3-(2'-methylphenyl) propan-1-ol, 2-ethyl-3-(4'-methylphenyl) propan-1-ol, 3-(3',4'-dimethylphenyl)-2-ethylpropane-1-ol, 2-ethyl-3-(4'-methoxyphenyl) propan-1-ol, 3-(3',4'-dimethoxyphenyl)-2-ethylpropane-1-ol, 2-allyl-3-phenylpropane-1-ol and 2-n-pentyl-3-phenyl-propan-1-ol.

As contemplated herein, the preferred deodorant active ingredients are odor absorbers, deodorizing ion exchangers, germ-inhibiting agents, prebiotically active components as well as enzyme inhibitors or, particularly preferred, combinations of the named active ingredients. Silicates serve as odor absorbers, which at the same time favorably support the rheological properties of the composition as contemplated herein. As contemplated herein, the most preferred silicates are phyllosilicates, montmorillonite, kaolinite, ilite, beidellite, nontronite, saponite, hectorite, bentonite, smectite, calcium silicates and talc.

Other preferred odor absorbers include zeolites, zinc cicinoleate, cyclodextrins, certain metal oxides and chlorophyll. Other odor absorbers preferred by the present disclosure are selected from pearlite. As contemplated herein, germ-inhibiting or antimicrobial agents are understood to be those agents which reduce the number of skin germs involved in the formation of odors or inhibit their growth. These germs include various species from the group of staphylococci, the group of corynebacteria, anaerocococci and micrococci.

As contemplated herein, organohalogen compounds as well as organohalides, quaternary ammonium compounds, several plant extracts and zinc compounds are preferred as germicidal or antimicrobial agents. These include triclosan, chlorhexidine and chlorhexidine gluconate, 3,4,4'-trichlorocarbanilide, bromochlorophene, dichlorophene, chlorothymol, chloroxylenol, hexachlorophene, dichloro-m-xylenol, dequalinium chloride, domiphene bromide, ammonium phenolsulfonate, benzalkonium halides, benzalkonium cetyl phosphate, benzalkonium saccharinates, benzethonium chloride, cetylpyridinium chloride, laurylpyridinium chloride, laurylisoquinolinium bromide, methylbenzethonium chloride. Furthermore, phenol, phenoxyethanol, disodium dihydroxyethylsulfosuccinylundecylenate, sodium bicarbonate, zinc lactate, sodium phenolsulfonate and zinc phenolsulfonate, ketoglutaric acid, terpene alcohols such as farnesol, chlorophyllin-copper complexes, α monoalkyl glycerol ether with a branched or linear saturated or unsaturated, optionally hydroxylated C6-C22 alkyl radical, particularly preferably α-(2-ethylhexyl)glycerol ether, commercially available as Sensiva® SC 50 (ex Schülke & Mayr), carboxylic acid esters of mono-, di- and triglycerol (e.g. (e.g. glycerol monolaurate, diglycerol monocaprinate), lantibiotics and plant extracts (e.g. green tea and components of lime blossom oil).

Further preferred deodorant active substances are selected from so-called prebiotically active components, by which as contemplated herein such components are to be understood which only or at least predominantly inhibit the odor-forming germs of the skin microflora, but not the desired, i.e. the non-odor-forming germs which belong to a healthy skin microflora. Explicit mention must be made here of active substances such as conifer extracts, in particular from the group of Pinaceae, and plant extracts from the group of Sapindaceae, Araliaceae, Lamiaceae and Saxifragaceae, in particular extracts of *Picea* spp., *Paullinia* sp., *Panax* sp., *Lamium album* or *Ribes nigrum*, and mixtures of these substances.

Other preferred deodorant active ingredients are selected from the germ-inhibiting perfume oils and the Deosafe® perfume oils available from Symrise, formerly Haarmann and Reimer.

Other preferred deodorant active substances are selected from silver salts, silver citrate, dihydrogen silver citrate, silver lactate and silver sulphate, soluble complex salts of silver, colloidal silver, and silver zeolites.

Enzyme inhibitors include substances which inhibit the enzymes responsible for sweat decomposition, arylsulfatase, β-glucuronidase, aminoacylase, esterases, lipases and/or lipoxigenase, e.g. trialkyl citric acid esters, triethyl citrate, or zinc glycinate.

Preferred deodorant emulsions as contemplated herein at least one deodorant active substance is selected from arylsulfatase inhibitors, beta-glucuronidase inhibitors, aminoacylase inhibitors, esterase inhibitors, Lipase inhibitors and lipoxigenase inhibitors, α monoalkylglycerol ethers with a branched or linear saturated or unsaturated, optionally hydroxylated C6-C22 alkyl radical, in particular α-(2-ethylhexyl) glycerol ether, phenoxyethanol, benzylheptanol, cocamidopropyl PG-dimonium chloride phosphate and butyloctanoic acid, polyglycerol-3-Caprylates, antibacterial perfume oils, Deosafe® perfume oils (Deosafe® is a registered trademark of Symrise, formerly Haarmann & Reimer), prebiotically active components, trialkyl citric acid esters, in particular triethyl citrate, active substances which reduce the number of skin germs from the group of staphylococci, corynebacteria, anaerocococci and micrococci involved in the formation of odors, or inhibit their growth, zinc compounds, in particular zinc phenolsulphonate and zinc cicinoleate, organohalogen compounds, in particular triclosan, chlorhexidine, chlorhexidine gluconate and benzalkonium halides, quaternary ammonium compounds, in particular cetylpyridinium chloride, odor absorbers, in particular silicates and zeolites, sodium bicarbonate, lantibiotics, and mixtures of the aforementioned substances.

The use of such active ingredients in the deodorant emulsion is advantageous, as they can give a deodorant additional effect as described in connection with the respective substances.

It is also preferred that the deodorant emulsion for an aerosol spray is free of decamethylcyclopentasiloxane.

Many cosmetics, especially deodorants and antiperspirants, contain the chemical compound decamethylcyclopentasiloxane, in short siloxane D5, as solvent. This siloxane is a volatile silicon compound and many users are concerned about its possible health effects. There is also controversy as to whether the substance should be classified as a PBT, i.e. as a persistent, bio-accumulative, and toxic substance that accumulates in the environment and whose effect on humans, if any, would be difficult to assess.

An already known problem is the accumulation of siloxanes in sewage and landfill sludge. The compound enters these via the sewage and waste cycle. During the combustion of sewage and landfill gases, e.g. in gas engines for energy generation, silica ("sand") is produced, which leads to premature wear of the combustion engines and to high costs for gas treatment.

For the reasons given above, it is desirable to dispense with decamethylcyclopentasiloxane and the inventors have succeeded in providing a formulation which makes this possible.

Furthermore, the present disclosure relates to a deodorant aerosol spray product comprising a pressure or pump spray container with a spray head, the filling of which comprises a deodorant emulsion as contemplated herein or preferred as contemplated herein and optionally a propellant and/or further solvent.

The provision of the aerosol spray product as contemplated herein has the advantage that the advantages described above can be experienced by a user in a particularly practical way that is suitable for everyday use. For example, many users appreciate the fresh feeling when spraying and the even distribution.

Furthermore, the present disclosure relates to the use of the deodorant aerosol spray product for deodorizing human skin as contemplated herein or the preferred deodorant spray product as contemplated herein.

The use as contemplated herein or preferred use as contemplated herein has the advantage that the advantages described above can be experienced by a user in a particularly practical and everyday way. For example, many users appreciate the fresh feeling when spraying and the even distribution.

Unless otherwise indicated in detail at the relevant place, the following definitions shall apply to the context of the present disclosure:

The term antiperspirant deodorant is not used quite uniformly in the field of cosmetics. Basically, an antiperspirant is usually understood to be a product designed to reduce or stop sweating and a deodorant is usually understood to be a product designed to reduce or stop the spread of unpleasant odors, for example by preventing the formation of bad smelling substances or by superimposing odors, binding or decomposing them.

The statement "free from" and comparable statements should mean that a substance, mixture of substances or product to which the statement relates is essentially free of the substance to which the statement also relates, i.e. to the extent that the thematic advantageous effect is achieved or as far as free of it, as is common in the technical field and can be achieved with the usual technical effort.

In the case of compounds of which both salt and acid forms are common, the specification of one form should include the other form. For example, the following shall apply: N,N-bis(carboxylatomethyl)-L-glutamate and/or methylglycinediacetic acid include the respective salt forms, in sodium salts and acid forms.

A spray in the context of the present disclosure, an aerosol spray is a spray which generates an aerosol. It can be a spray with propellant, which is common in the deodorant sector, or a pump spray, which is less common but preferred by certain users, for example because it is easier to transport, for example when travelling by plane, or because it is generally preferred to release as little propellant as possible into the living environment and, ultimately, the atmosphere.

A salt as contemplated herein is any cosmetically acceptable salt. Compounds that are in salt form, but where properties dominate that are not due to their salt property, can be designated differently and placed in a different category without negating their salt property or changing the definition of a salt.

If at one point of this patent application an ingredient is mentioned which can be assigned to a certain substance class, e.g. salts, but which is dealt with on its own or in a smaller group, and at another point comments are made on just this substance class, this may mean, depending on the wording, that an additional representative of the substance class must be present or that the respective condition can also be fulfilled by the aforementioned substance alone.

An inventive example of a combination of a blowing agent with a generally held emulsion (also called brew or base formulation) is:

| Content | Percentage [weight %] |
|---|---|
| Propane, butane 15:85 (2.1 bar) | 80.00 |
| Deo emulsion deodorant spray (basic formulation)-SUD | 20.00 |

An invented example of a deodorant emulsion is:

| Ingredient | Percentage [weight %] |
|---|---|
| Triethyl citrate | 6.0 |
| 2-ethylhexyl palmitate | 7.42 |
| Dimethicone 5 cSt | 10.00 |
| Phenoxyethanol, pure | 1.00 |
| Dow Corning ES-5227 DM Formulation Aid | 2.80 |
| Water, demineralized | 30.28 |
| Magnesium sulfate * 7H$_2$O, ultra-pure | 2.50 |
| Propandiol-1,2 | 35.00 |
| Perfume Crispy Grapefruit A T12033987 | 5.00 |

An example as contemplated herein is a combined filling of deodorant emulsion and propellant gases, as it can be contained in an emulsion spray:

| Content | Percentage [weight %] |
|---|---|
| Propane, butane 15:85 (2.1 bar) | 80.00 |
| Triethyl citrate | 1.20 |
| 2-ethylhexyl palmitate | 1.48 |
| Dimethicone 5 cSt | 2.00 |
| Phenoxyethanol, pure | 0.20 |
| Dow Corning ES-5227 DM Formulation Aid | 0.56 |
| Water, demineralized | 6.06 |
| Magnesium sulfate * 7H$_2$O, ultra-pure | 0.50 |
| Propandiol-1,2 | 7.00 |
| Perfume Crispy Grapefruit A T12033987 | 1.00 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A deodorant emulsion suitable for an aerosol spray comprising:
at least one emulsifier;
at least one salt;

a water/alcohol mixture, wherein the alcohol is selected from propanol, isopropanol, propanediol-1,3, dipropylene glycol, propanediol-1,2, or a combination thereof;
at least one silicone oil; and
at least one further oil;
wherein the deodorant emulsion is free from aluminum salts and ethanol.

2. A deodorant emulsion according to claim 1, comprising:
from about 1.0% to about 4.5% by weight of the at least one emulsifier,
from about 0.5% to about 7.0% by weight of the at least one salt,
from about 3.0% to about 17.0% by weight of the at least one silicone oil, and
from about 6.0% to about 17.0% by weight of the at least one further oil,
all based on the total weight of the deodorant emulsion.

3. A deodorant emulsion according to claim 2, further comprising at least one perfume oil in a concentration of from about 2.0% to about 8.0% by weight, based on the total weight of the deodorant emulsion.

4. A deodorant emulsion according to claim 1, comprising:
from about 2.0% to about 4.0% by weight of the at least one emulsifier,
from about 1.0% to about 5.0% by weight of the at least one salt,
from about 5.0% to about 15.0% by weight of the at least one silicone oil, and
from about 11.0% to about 15.0% by weight of the at least one further oil,
all based on the total weight of the deodorant emulsion.

5. A deodorant emulsion according to claim 4, further comprising at least one perfume oil in a concentration of from about 3.0% to about 7.0% by weight, based on the total weight of the deodorant emulsion.

6. A deodorant emulsion according to claim 1, further comprising at least one perfume oil in a concentration of from about 1.0% to about 10.0% by weight, based on the total weight of the deodorant emulsion.

7. A deodorant emulsion according to claim 1, wherein the deodorant emulsion further comprises at least one deodorant active ingredient in a concentration of 0.1% to 50.0% by weight, based on the total weight of the deodorant emulsion.

8. A deodorant emulsion according to claim 1, wherein the deodorant emulsion is free of decamethylcyclopentasiloxane.

9. A deodorant emulsion according to claim 1, wherein the water/alcohol mixture is included in an amount of from about 60% to about 99% by weight based on the total weight of the deodorant emulsion.

10. A deodorant emulsion according to claim 1, wherein:
the at least one emulsifier comprises a silicone emulsifier; and
the at least one salt is a magnesium sulfate;
the at least one silicone oil is selected from linear silicone oils or cyclic silicone oils.

11. A deodorant emulsion according to claim 1, wherein:
the at least one emulsifier is an alkoxylated fatty acid alcohol,
the at least one salt is a magnesium sulfate;
the at least one silicone oil is selected from polydimethylsiloxane or cyclopentasiloxane.

12. A deodorant aerosol spray product comprising a pressure or pump spray container with spray head, the deodorant emulsion according to claim 1, wherein the deodorant emulsion optionally comprises a propellant and/or a further solvent.

13. A method comprising applying the deodorant aerosol spray product according to claim 12 to human skin.

14. A deodorant emulsion according to claim 1, comprising:
from about 2.0% to about 4.0% by weight of the at least one emulsifier,
from about 1.0% to about 5.0% by weight, of the at least one salt;
from about 5.0% to about 15.0% by weight of the at least one silicone oil; and
from about 11.0% to about 15.0% by weight of the at least one further oil;
wherein all amounts are based on the total weight of the deodorant emulsion.

15. A deodorant emulsion according to claim 1, wherein the alcohol is propanediol-1,2.

16. A deodorant emulsion according to claim 1, wherein the water/alcohol mixture is included in an amount of from about 65% to about 96% by weight, based on the total weight of the deodorant emulsion.

17. A deodorant emulsion comprising:
triethyl citrate and phenoxyethanol;
dimethicone;
a dispersion of silicone polyether in a low-viscosity, non-volatile dimethicone liquid;
a water/propanediol-1,2 mixture; and
magnesium sulfate;
wherein the deodorant emulsion is free from aluminum salts and ethanol.

18. A deodorant emulsion according to claim 17, comprising:
the triethyl citrate and phenoxyethanol in a combined amount of from about from about 1.0% to about 30.0% by weight;
the dimethicone in an amount of from about 5.0% to about 15.0% by weight;
the dispersion of silicone polyether in a low-viscosity, non-volatile dimethicone liquid as a 25% dispersion of silicone polyether in a low-viscosity, non-volatile dimethicone liquid with the INCI name Dimethicone (and) PEG/PPG-18/18 Dimethicone in an amount of from about 2.0% to about 4.0% by weight;
the water/propanediol-1,2 mixture in an amount of from about 65% to about 96% by weight; and
the magnesium sulfate in an amount of from about 1.0% to about 5.0%-by weight.

* * * * *